United States Patent [19]

Rosolia

[11] Patent Number: 5,463,908
[45] Date of Patent: Nov. 7, 1995

[54] APPARATUS FOR SAMPLING AND REGISTERING FLUIDS IN PIPELINES

[76] Inventor: Antonio Rosolia, P.O. Box 80, Artois, Calif. 95913

[21] Appl. No.: 247,217

[22] Filed: May 20, 1994

Related U.S. Application Data

[63] Continuation-in-part of Ser. No. 37,350, Mar. 29, 1993, abandoned.

[51] Int. Cl.[6] ................................................... G01N 1/14
[52] U.S. Cl. ........................................................ 73/863.83
[58] Field of Search .......................... 73/863.81–863.86, 73/863.33, 864.34, 864.35, 863.51–863.58, 863.02, 863.03, 864.73, 864.74, 866.5, 863.83

[56] References Cited

U.S. PATENT DOCUMENTS

| | | |
|---|---|---|
| 2,906,126 | 9/1959 | Brown . |
| 3,007,340 | 11/1961 | Kraftson . |
| 3,085,435 | 4/1963 | Miscoe et al. ................. 73/863.81 |
| 3,555,910 | 1/1971 | Spence et al. . |
| 3,672,225 | 6/1972 | Louis ............................. 73/863.58 |
| 3,784,902 | 1/1974 | Huber ............................ 73/863.03 |
| 3,803,921 | 4/1974 | Dieterich ...................... 73/863.51 |
| 4,346,609 | 8/1982 | Diesel . |
| 4,346,611 | 8/1982 | Welker .......................... 73/866.5 |
| 4,485,684 | 12/1984 | Weber et al. ................. 73/863.86 |
| 4,557,151 | 12/1985 | Welker .......................... 73/863.84 |
| 4,562,749 | 1/1986 | Clark ............................. 73/863.84 |
| 4,625,571 | 12/1986 | Slater ............................ 73/863.84 |

FOREIGN PATENT DOCUMENTS

| | | |
|---|---|---|
| 92000011 | 3/1992 | Italy . |
| 397803 | 2/1974 | U.S.S.R. . |

*Primary Examiner*—Robert Raevis
*Attorney, Agent, or Firm*—Janet Kaiser Castaneda; James E. Eakin

[57] ABSTRACT

An apparatus for sampling and registering fluids in pipelines utilizes a single probe to monitor fluid flow characteristics using sensors and attached gauges while simultaneously collecting fluid samples for laboratory analysis. A hollow probe defining fluid flow openings and a sample opening extends into the pipeline, and a pneumatically driven sampling assembly is slidingly engaged within the probe to carry the fluid sample through a fluid channel to a sample collection device. The fluid flow openings carry fluid through separate channels having sensors to gauges to simultaneous monitor the fluid flow rate and/or temperature. A variety of monitoring devices may be attached to the sampling apparatus, including on-line analyzers, thermocouple devices, pressure transmitters, and virtually any computerized monitoring device.

11 Claims, 8 Drawing Sheets

APPARATUS FOR SAMPLING AND REGISTERING FLUIDS IN PIPELINES

RELATED APPLICATIONS

This application is a continuation-in-part of U.S. patent application Ser. No. 08/037,350, filed on Mar. 29, 1993, now abandoned.

TECHNICAL FIELD

The present invention relates to devices for sampling and measuring physical data in fluids within pipelines. More particularly, the invention relates to a sampling apparatus, connected to a pipeline by a standard fitting and able to be attached to a variety of gauges and computers or other memory devices, that collects accurate samples of fluids in one receiver for analytical work and at the same time obtains a full range of data regarding the fluid physics within the pipeline, such as flow rate, pressure and temperature.

BACKGROUND OF THE INVENTION

Devices for sampling and measuring data in fluids within pipelines are well known in the prior art. Such devices typically are single gauge devices, monitored locally, and limited to obtaining samples for a single test. Prior art fluid sampling devices are generally not useful with multiple gauges or for transferring data for processing by computers or other memory devices.

One such single gauge prior art sampling device described in U.S. Pat. No. 3,555,910 expels sampled particles from a sampling probe into a container by applying a blast of air from a separate pneumatic system mounted above the probe. In the '910 system, a bracket on the moveable cylinder of the separate pneumatic system engages a bracket of the probe, thereby actuating the sampling motion of the probe with movement of the cylinder.

Other single gauge sampling probes are described in USSR Patent No. 397,803 which utilizes a perforated tube for averaging collected samples, and in U.S. Pat. No. 3,007,340 which inserts the detecting element directly into the fluid to be monitored.

Other prior art sampling probes driven by a turbine installed through a second opening in the pipeline are described in U.S. Pat. No. 4,346,609 and 2,906,126.

A heretofore unmet need exists for apparatus for sampling fluid in a pipeline using a single probe mounted through the wall of the pipeline and able to collect multiple samples to measure a variety of fluid characteristics using multiple gauges and/or computerized monitoring systems.

SUMMARY OF THE INVENTION WITH OBJECTS

A general object of the invention is to provide an apparatus for sampling fluids in pipelines that overcomes the limitations and drawbacks of the prior art.

A specific object of the invention is to provide an apparatus for sampling fluids in pipelines that is accurate, fast, and collects multiple samples for laboratory analysis.

Another specific object of the invention is to provide an apparatus for sampling fluids in pipelines which minimizes the effects of turbulence from the presence of other probes in the vicinity of the sampling apertures.

One more specific object of the invention is to provide an apparatus for sampling fluids in pipelines which minimizes flow resistance in the pipeline thereby increasing energy effectiveness.

Yet another specific object of the invention is to provide an apparatus for sampling fluids in pipelines which is easily installed utilizing one standard connection to affix the apparatus to the pipeline.

Still another specific object of the invention is to provide an apparatus for sampling fluids in pipelines which acts as a flow sampling device capable of interfacing with computerized monitoring systems.

Yet one more specific object of the invention is to provide an apparatus for sampling fluids in pipelines enabling sample collection for delivery to multiple gauges and computerized monitoring systems to provide a plurality of fluid characteristic specifications.

Still one more specific object of the invention is to provide an apparatus for sampling fluids in pipelines that simultaneously measures differential pressure and/or temperature within a pipeline while collecting a separate sample which may be used to determine multiple fluid parameters.

An apparatus for sampling fluids in pipelines is provided to enable a single probe to measure and register a variety of fluid characteristics. The sampling apparatus monitors fluid flow characteristics using sensors and attached gauges while simultaneously collecting fluid samples for laboratory analysis.

The sampling apparatus includes a housing attached to a flange or other standard connection or fitting which defines an aperture therethrough and is securely fastened to an opening in the wall of the pipeline to be monitored. A hollow probe rod secured to the flange extends into the pipeline.

A reciprocating piston assembly is mounted within the housing for operation of the sampling assembly which is slidingly engaged within the hollow rod. In addition to the hollow rod, the sampling assembly includes three hollow components: an internal bar slidably engaged against the interior wall of the hollow rod, a plunger tube slidably engaged within the internal bar, and a flushing tube mounted within the plunger tube. An annular space is provided between the flushing tube and the plunger tube, and the flushing tube defines a terminal end capable of closing off the annular space. Sample apertures in the exterior wall of the hollow rod and the internal bar, when aligned, enable fluids to enter and pass through the sample assembly prior to being isolated for pressurized delivery through the annular space into a sample collection device via an outlet in the housing.

A plurality of grooves in the probe rod are provided to simultaneously monitor the fluid flow rate and/or temperature via pressure sensors coupled at two separate, communicating longitudinal fluid channels for upstream and downstream fluid intake, and a thermocouple mounted inside the flushing tube.

A variety of monitoring devices may be attached to the sampling apparatus, including on-line analyzers, thermocouple devices, pressure transmitters, and virtually any computerized monitoring device.

These and other objects, features, aspects and advantages of the present invention will be more fully apparent to those skilled in the art upon consideration of the following detailed description of the preferred embodiments, presented in conjunction with the accompanying drawings.

BRIEF DESCRIPTION OF THE DRAWINGS In the Drawings.

DETAILED DESCRIPTION OF PREFERRED EMBODIMENTS

Figure 1:
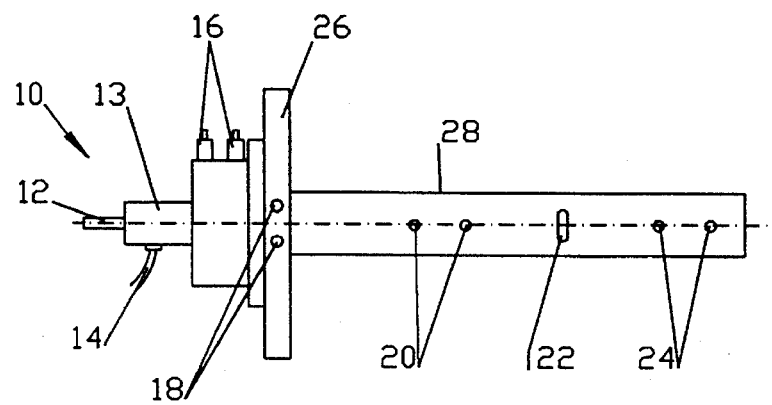
FIG. 1 is a side view of a sampling apparatus embodying the principles of the present invention.

An apparatus for sampling fluids in pipelines and embodying the principles of the present invention is shown generally at reference number 10 in FIGS. 1 through 4.

The devices for attaching equipment to the sampling apparatus 10 are described first and include a purge coupling 12 for flushing the apparatus 10 between samples (or for connecting an ancillary measuring device), a sample outlet coupling 14 for transferring collected fluids to a collection device for laboratory testing purposes, dual air couplings 16 providing air pressure and exhaust sides, and dual transmitter couplings 18 for connection to, for example, a differential pressure transmitter. With the exception of transmitter couplings 18, all of the above described couplings extend into a hollow tubular housing defining an upper housing portion 13 and a lower housing portion 15.

Figure 2:
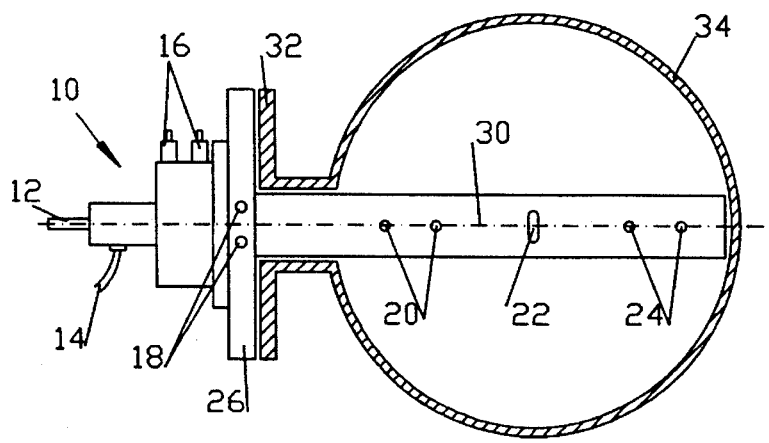
FIG. 2 is a diagrammatic view, partially in section, showing the sampling apparatus of FIG. 1 attached to a pipeline.
Figure 3:
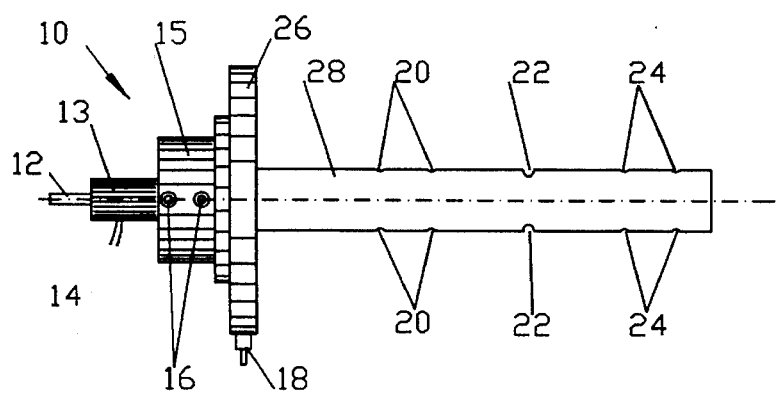
FIG. 3 is a side view of the sampling apparatus of FIG. 1 showing further details of the sample distribution connector end.
Figure 4:
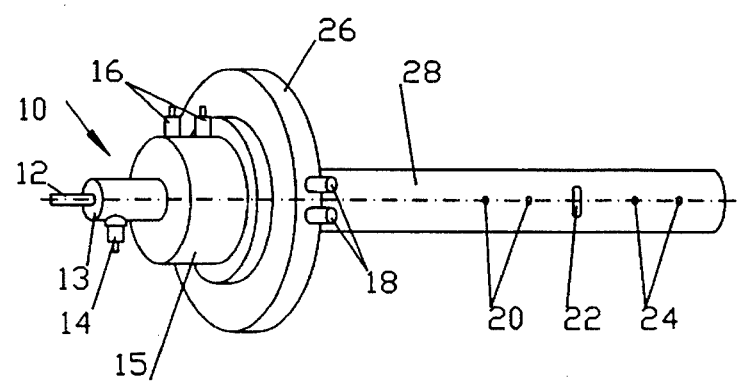
FIG. 4 is a perspective view of the sampling apparatus of FIG. 1.

The lower housing 15 is affixed to an annular flange 26 which is, in the embodiment shown, preferably a 3-inch flange, number 150 ANSA R. F. or equivalent. It will be recognized by those skilled in the art that the flange is a standard connector which may be modified and shaped according to the configuration of the sampling apparatus and the pipeline to be sampled. As shown in FIG. 2, flange 26 is attached to a pipe flange 32, which extends from pipe 34, using bolts extending through mating bolt holes 17 in flange 32 and flange 26. (See FIGS. 5 and 6). Transmitter couplings 18 extend into the flange 26, and mating central openings in the flanges 26, 34 provide access to the interior of the pipe 34.

A hollow probe rod 28 surrounding the opening on the mounting face of the flange 26 extends therefrom through the central opening in the pipe flange 32 to span the center of the pipe 34 where it is centrally disposed perpendicular to the axis of the pipe 34. The probe rod 28 defines at least one enlarged sample inlet 22 extending therethrough and a plurality of Pitot openings 20 (inner openings) and 24 (outer openings).

Figure 5:
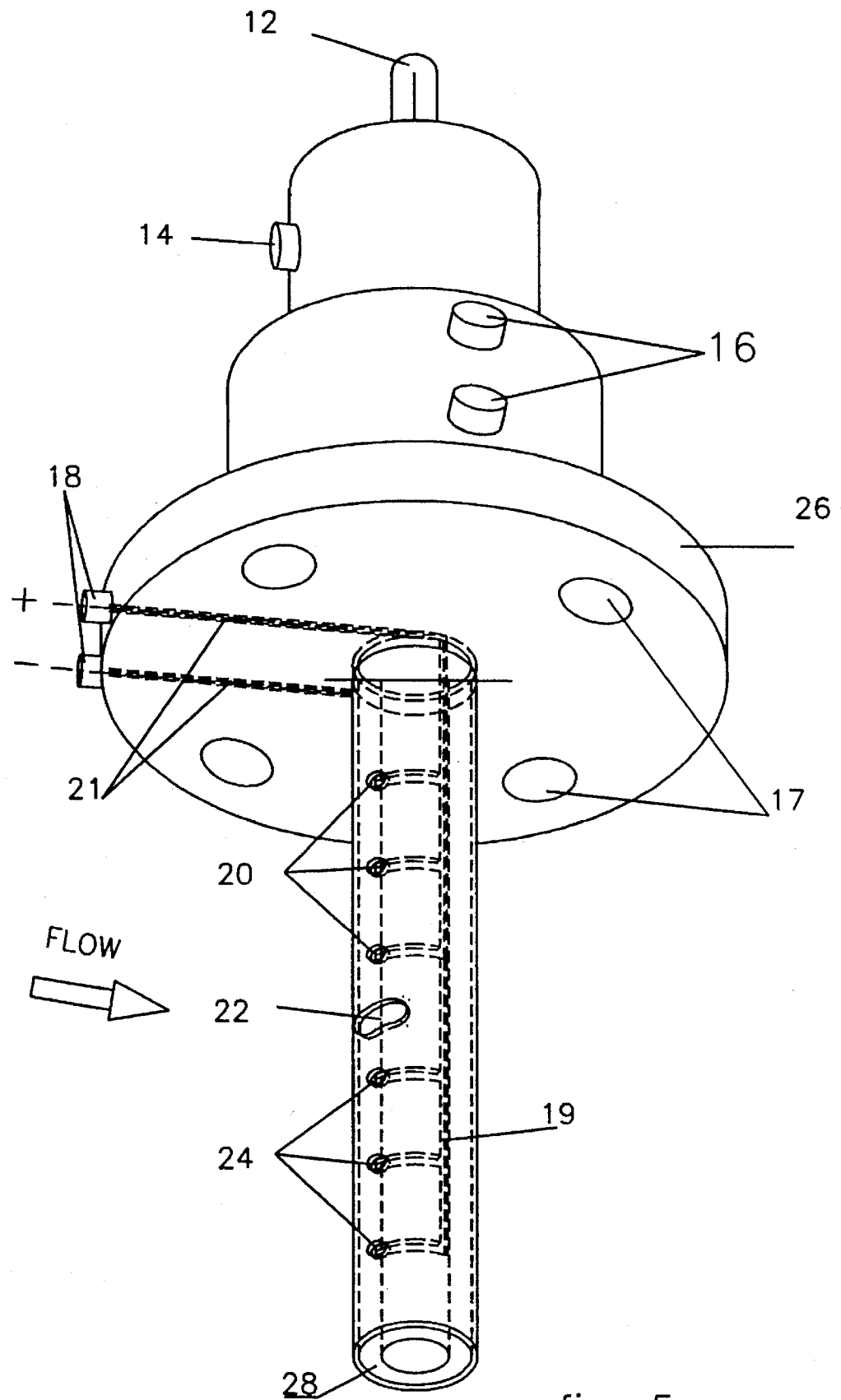
FIG. 5 is a diagrammatic view of the sampling apparatus showing in dashed lines the upstream internal channel communication with a differential pressure gauge, and showing the sample apertures.
Figures 6, 6A:
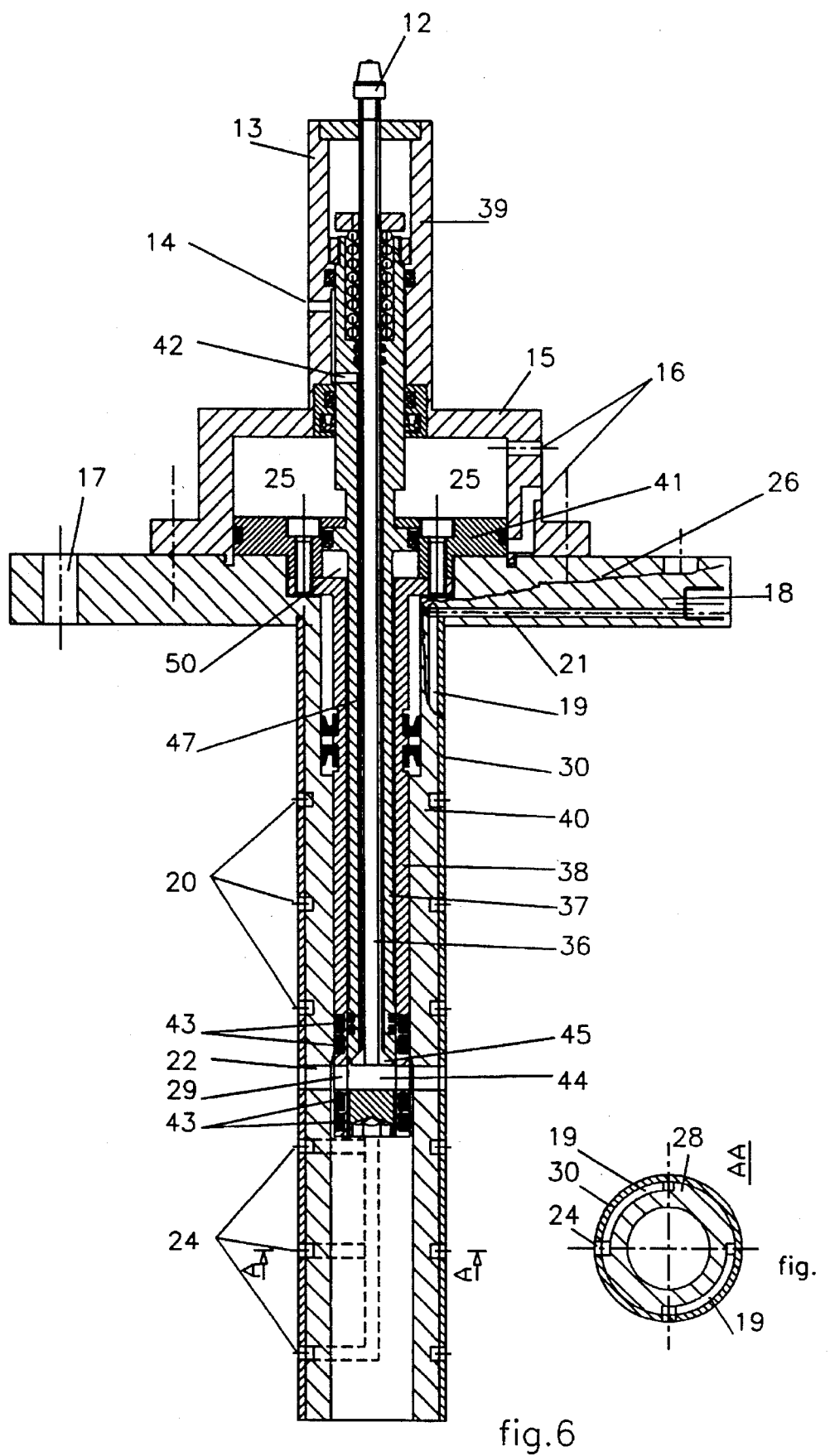
FIG. 6 is an enlarged cross sectional view of the sampling apparatus of FIG. 1 shown with the sampling assembly fully extended into the hollow rod thereby allowing the fluid in the pipeline to flow through the hollow rod.
FIG. 6A is a cross sectional view taken along the lines A—A in FIG. 6 and showing the Pitot holes and symmetrical channels.

Referring now to FIG. 6, the transverse Pitot openings 20, 24 upstream and downstream connect respectively to two longitudinal grooves 19 formed in the exterior surface of probe rod 28 and covered by liner 30, as best shown in FIGS. 5 and 6A. The Pitot openings 20, 24 enable fluid to be monitored for flow and differential pressure by the differential pressure via transmitter couplings 18. A differential fluid pressure sensor is mounted on the external end of upstream and downstream grooves 19, and a thermocouple to provide temperature control is mounted inside the flushing tube. The differential pressure gauge or transmitter measures the mean differential pressure between the upstream and downstream grooves 19 to also monitor the flow rate.

FIG. 6 illustrates details of the sampling assembly which, in the embodiment shown, is pneumatically operated by piston 41 in response to air provided and exhausted through air lines 16. It will be recognized by those skilled in the art that other gases, or even liquids may be used to operate piston 41.

The piston 41 is mounted for reciprocation in the interior chamber 25 of housing 15. Bolted to the bottom of the piston 41 is a hollow internal bar 38 which slidingly engages with the inner surface of the hollow rod 28. A mating sample inlet 29, when aligned with sample inlet 22 in the probe rod 28, enables fluid flowing through the pipe to pass through the sampling apparatus 10. Seal rings 43 are provided above and below the mating sample inlet 29 to assure that a uniform volume of fluid is collected regardless of changes in the fluid pressure in the pipe 34.

Mounted within the internal bar 38 is a plunger tube 37 which is also hollow and which extends through an opening in the piston 41 into the upper housing portion 13 to plunger stop 39. The plunger tube 37 reciprocates with the piston 41 and further reciprocates in a chamber 50 formed between the piston 41 and the internal bar 38 attached thereto.

Mounted inside of the hollow plunger tube 37 is a hollow flushing tube 36. A annular space 47 between the plunger tube 37 and the flushing tube 36 communicates with channel outlet 42 which, when aligned with sample outlet 14, enables delivery of sample to a collection device. (See FIGS. 10 and 11). At the terminal end of the flushing tube 36 is welded a shutter 45 with sloping sides having a mating geometry for seating against the sloping sides provided at the internal end of plunger tube 37. When the shutter 45 is seated against the end of plunger tube 37, fluid is prevented from entering the annular space 47.

Figure 8:
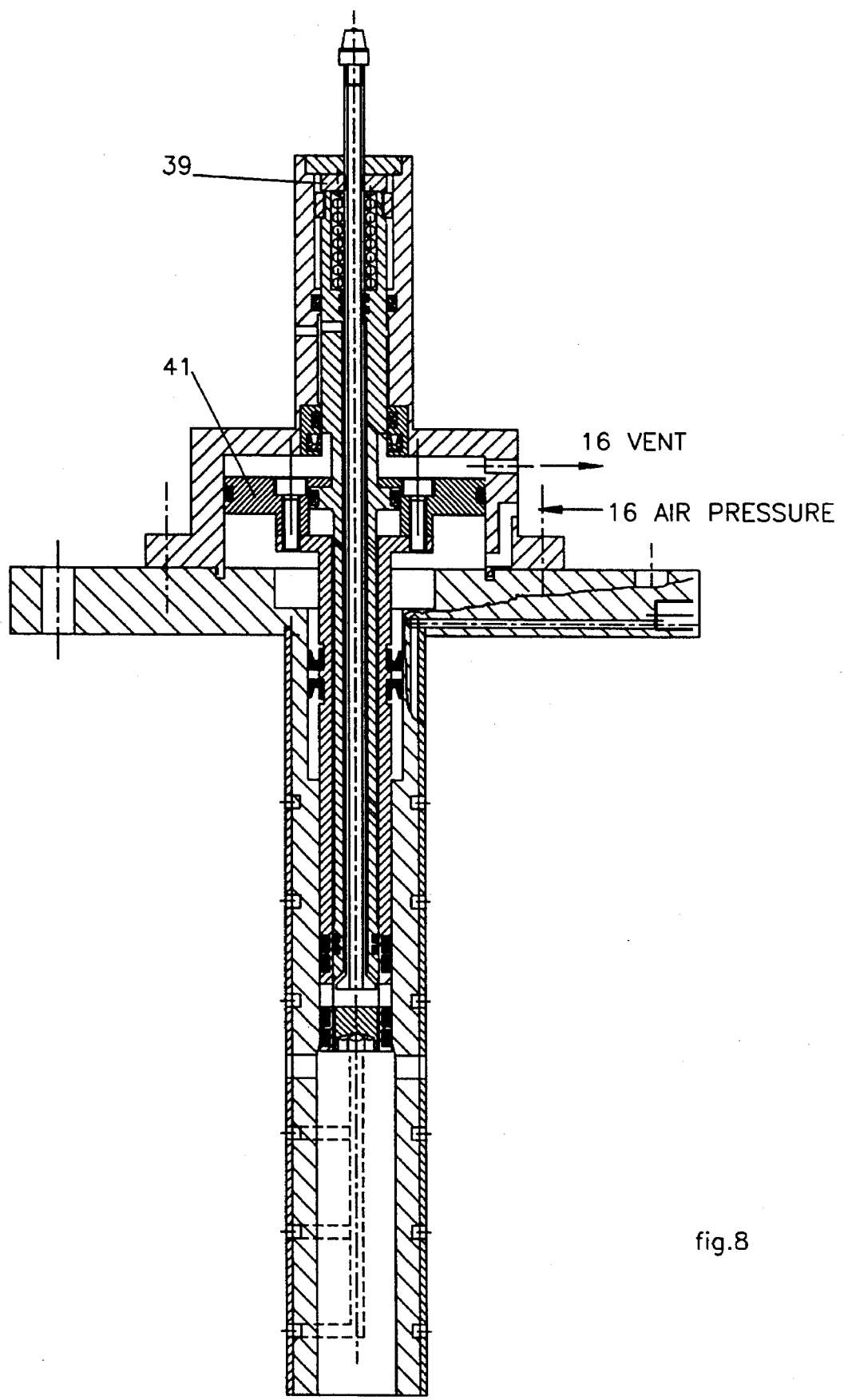
FIG. 8 is an enlarged cross sectional view of the sampling assembly of FIG. 1 shown with the terminal end extended prior to forcing the collected fluid through the fluid channels.
Figure 9:
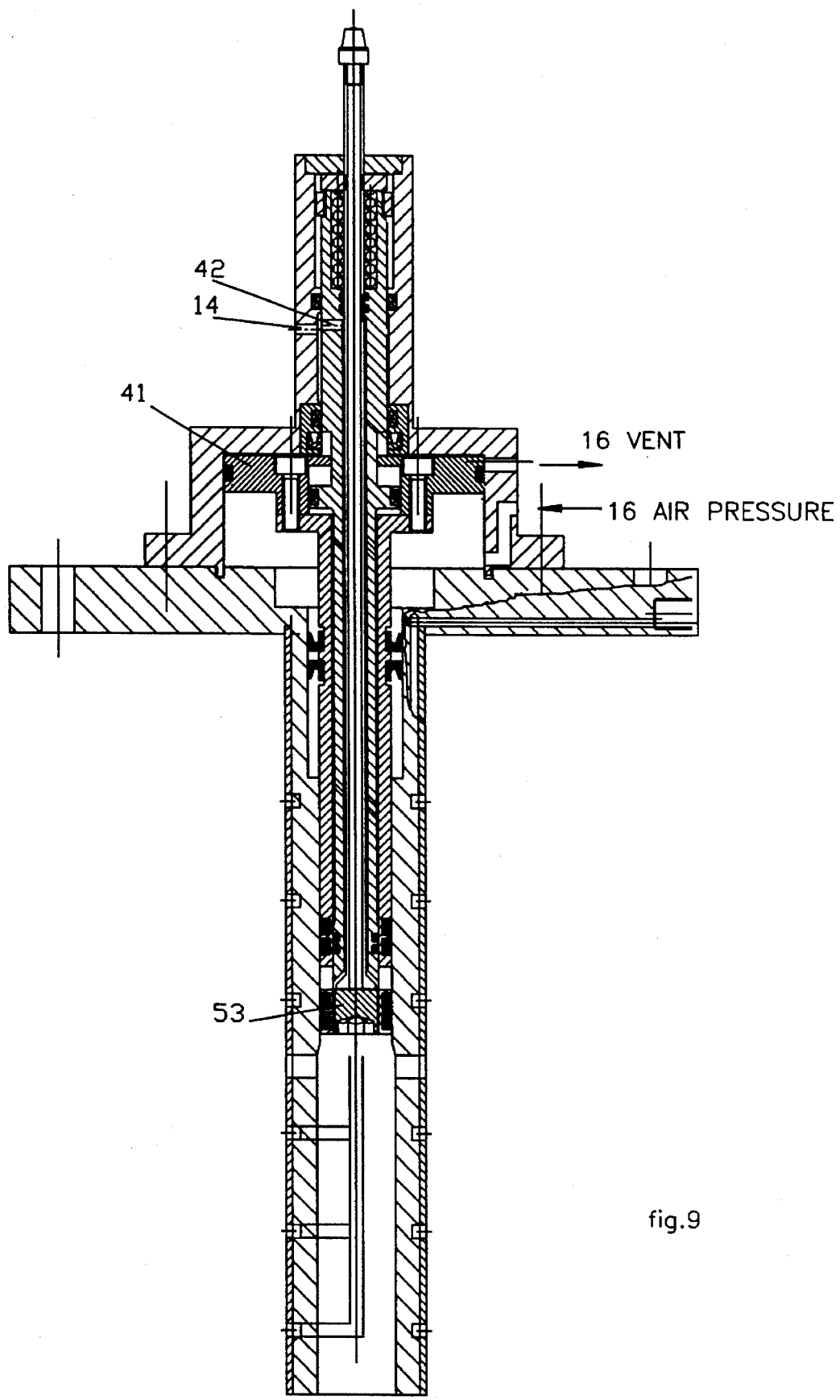
FIG. 9 is an enlarged cross sectional view of the sampling assembly of FIG. 1 shown in the position of expelling the collected fluid to the sample outlet for transfer to sample collection device.
Figure 10:
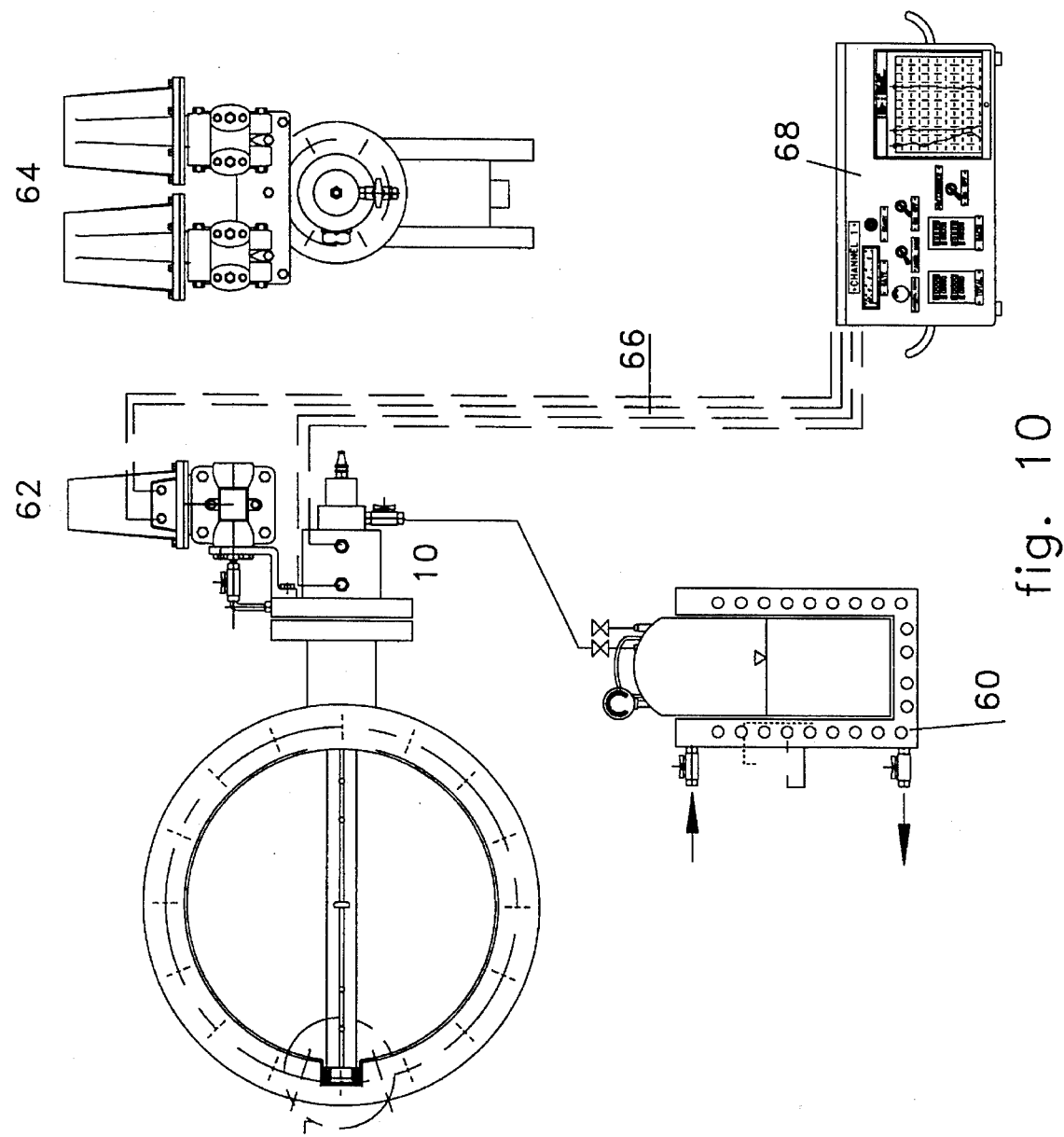
FIG. 10 is an environmental view showing the sampling apparatus operated by a steam conditioner, attached to a differential pressure transmitter, or alternately, to a differential pressure and temperature transmitter, and cable connected to a remote control unit.
Figure 11:
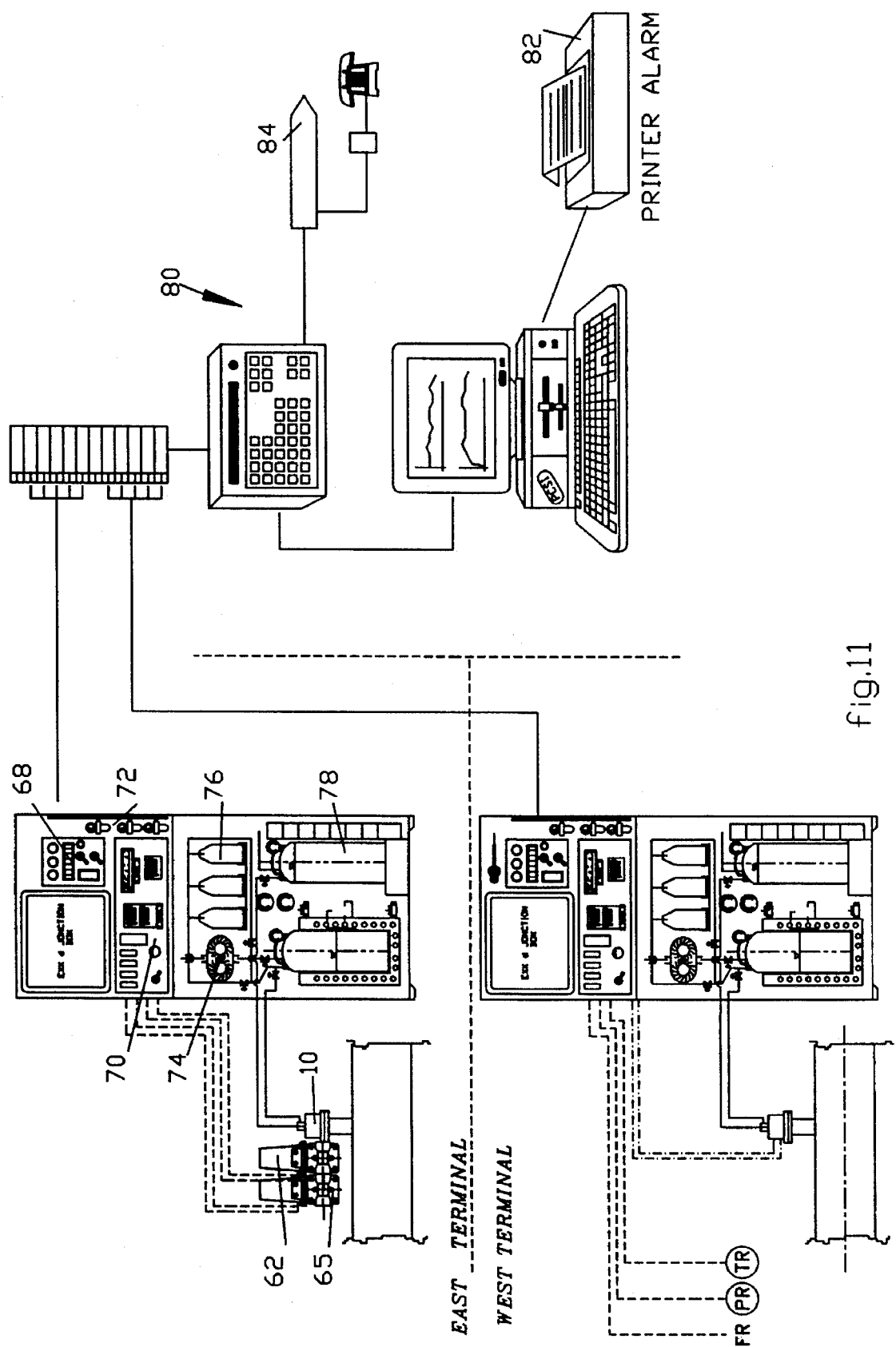
FIG. 11 is an environmental view showing two sampling units attached to local control units which are, in turn, controlled by a remote computerized system having alarm and annunciator capability.

Operation of the sampling assembly (using flushing tube 36, plunger tube 37, internal bar 38, plunger stop 39, and probe rod 40) to obtain a sample of fluid from the pipe 34 is illustrated in FIGS. 6 through 9 and assumes connection of the apparatus 10 to the proper air supply and differential analyzers so that apparatus 10 is ready for operation, for example, as shown in FIGS. 10 and 11. The intermittent sampling operation occurs simultaneously with the differential pressure measurement described earlier and occurring via the pitot openings 20, 24, the upstream and downstream grooves 19, and the differential pressure gauge.

When sufficient air pressure is provided to the chamber 25 above the piston 41 so that the piston is in its lowermost position as shown in FIG. 6, sample inlets 22, 29 are aligned, allowing the fluid flowing through the pipe 34 to pass through and exit the probe rod 28. The plunger tube 37 is in its uppermost position within chamber 50, and the shutter 45 is seated against the plunger tube 37 thereby closing off annular space 47. FIG. 6 represents the stand-by position.

Figure 7:
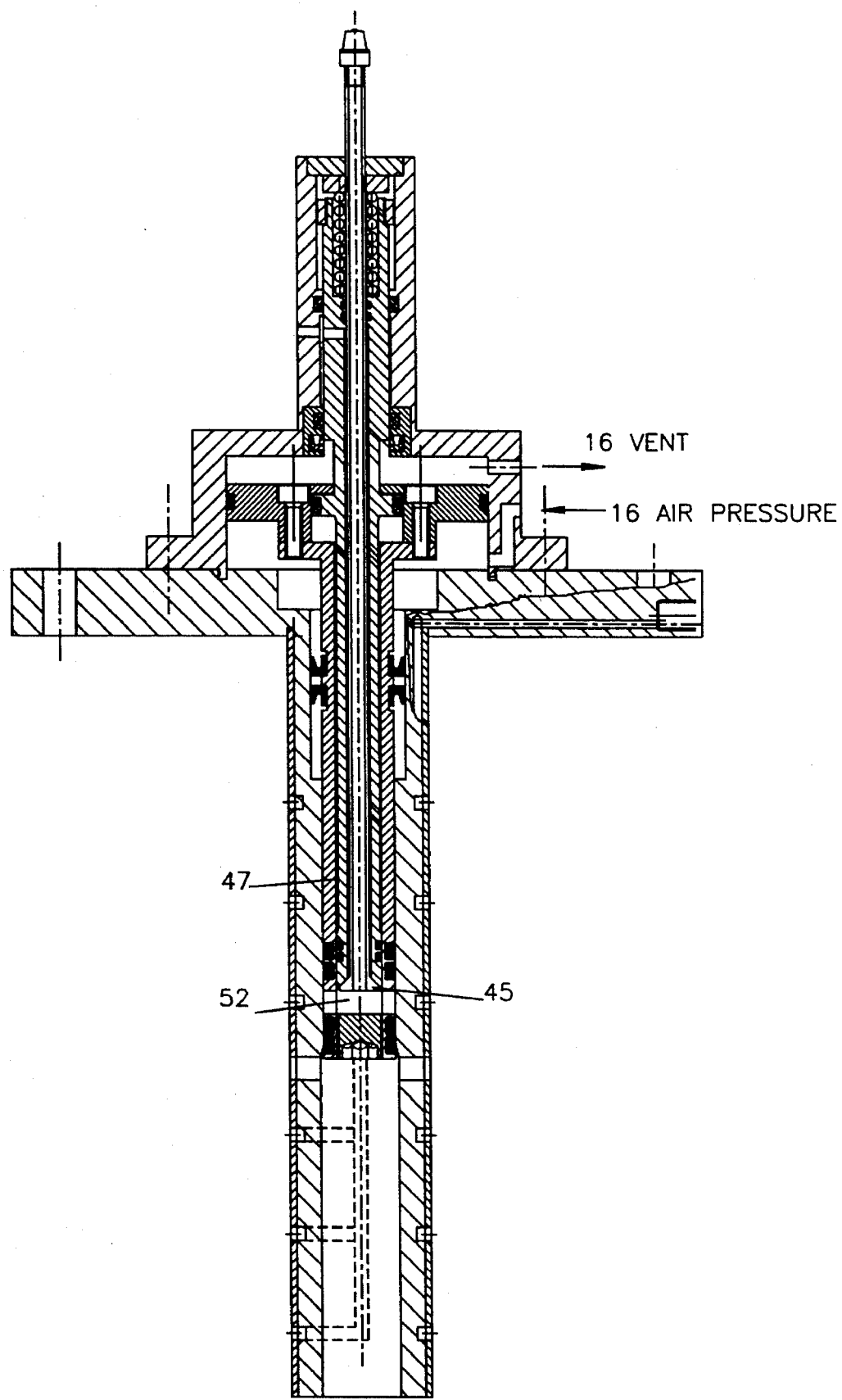
FIG. 7 is an enlarged cross sectional view of the sampling apparatus of FIG. 1 shown with the sampling assembly partially retracted and the sample confined below the terminal end of the flushing tube.

Referring now to FIG. 7, the piston 41 has moved upwardly in chamber 25, in response to air supplied below the piston according to the directional arrows 18, and the structures defined by reference numerals 36, 37, 38, and 39 move upwardly with the piston 41 thereby shutting off, in sequence, the openings at 22, 29 to isolate a sample of fluid in created fluid cell 52. The shutter 45 remains seated thereby preventing the sample, generally several milliliters in size, from entering the annular space 47. The volume of the sample intermittently collected in the fluid cell 52 is accurate each time.

In FIG. 8, the piston 41 has moved slightly upwardly, and plunger tube 37 is locked in its uppermost position, thereby causing the shutter 45 to open. In FIG. 9, since the internal bar 38 continues to move until the piston 41 has reached its uppermost position and the plunger tube has already reached its uppermost position, the terminal end 53 of the internal bar 38 moves towards the shutter 45 and compresses the fluid sample into the annular channel 47 between the flushing tube 36 and the plunger tube 37. The fluid passes through the annular space 47 to channel outlet 42 for exit through sample outlet 14.

Following sampling, coupling 12 may be used to deliver cleaning fluid through flushing tube 36 to exit 14. During sampling, coupling 12 may be connected to an additional analyzer, or it may be closed off.

The sampling apparatus 10 may be utilized for sampling fluids from a variety of pipelines, such as the pipelines used to transfer hydrocarbons, or the pipelines used in hydroelectric plants. Water taken from a river or lake and directed to power a generator turbine in a hydroelectric plant contains impurities which must be identified and quantified. Crude oil transferred from a ship to a storage plant has specific physical characteristics and will contain a percentage of water. Cargoes of crude oil are sold on the basis of clean oil volume and the measurement of water content is generally determined by inaccurate sounding techniques. The sampling apparatus provided enables accurate determination of the level of oil over water and the measurement of physical characteristics in pipeline fluids. Turbulence is minimized because only one sampling devices is required in the pipeline. Sampling apparatus 10 can be used in sampling operations according to the following standards: ISO 3172; ASPM D 477; API CAP 8.2; and BP 6.2.

As shown in FIG. 10, sampling apparatus 10 may be used in a pneumatic sampling system having a conventional steam conditioner 60, a differential pressure transmitter 62 (or a differential pressure transmitter and temperature transmitter 64), connected by a multiconductor cable 66 to a remote control unit 68. As shown in FIG. 11, the sampling apparatus may be electronically controlled. In the FIG. 11 configuration, multiple sampling apparatuses 10 are provided, each having differential pressure and temperature transmitters 62, 65, and each controlled by control units 68. The control units 68 may include pneumatic control 70, air supply regulators 72, a sample mixer 74, subsample collectors 76, and a purge reservoir 78. The control units 68 may be connected to a computerized control system 80 including a printer alarm 82 and an annunciator system 84. As demonstrated in FIGS. 10 and 11, only one probe is needed to provide several measurements. Prior to sampling operations, the operator merely needs to attach the desired analyzing system to the probe.

The apparatus described herein is illustrative of the principles of the invention and is not meant to be limiting of its scope. For instance, the internal mechanism to collect the sample from inlet 22, as shown in FIGS. 6, 6A, 7, 8 and 9 is only one of the possible mechanical utilizations and the collection and delivery of a small liquid sample to an external receiver can be made in several different ways. Various other embodiments will be apparent to those skilled in the art and may be made without departing from the spirit and scope of the invention as defined by the following claims.

What is claimed is:

1. An apparatus for sampling fluid flow in a conduit comprising:
   probe means adapted to be removably mounted within the conduit for collecting at least one sample having a fixed volume of fluid and for simultaneously monitoring at least one fluid property, the single probe means comprising:
   hollow housing means defining at least one passage therethrough;
   hollow piston means mounted for reciprocation within the housing means and defining an aperture therethrough, alignment of the at least one passage and the aperture occurring at at compression position having the piston means extended to enable fluid in the conduit to pass through the probe means, retraction of the piston means during a decompression stage causing misalignment of the aperture and the at least one passage for isolating the fixed volume of sample in a sample chamber;
   channel means communicating with the sample chamber and adapted to be connected to a collection device for delivery of the fixed column of sample thereto;
   shutter means mounted within the hollow piston means, a pressure of the fluid flow through the at least one passage, together with continued decompression to continue retraction, opening the shutter means to enable the fixed volume of sample to flow from the sample chamber into the channel means and into the collection device.

2. The apparatus of claim 1 further comprising means for simultaneously and continuously monitoring two fluid properties while simultaneously and intermittently collecting at least one sample.

3. The apparatus of claim 2 wherein the means for simultaneously monitoring the two fluid properties are a temperature sensor and a device for measuring differential pressure.

4. The apparatus of claim 3 wherein the device for measuring differential pressure comprises at least one upstream and downstream opening in the housing means communicating with, respectively, at least one upstream and downstream channel, the at least one upstream and downstream channel adapted for connection to a differential pressure gauge.

5. The apparatus of claim 4 wherein the probe means is adapted for connection to a computer means for controlling sampling and monitoring.

6. A device for collecting samples and data from a pipeline containing flowing fluids comprising:

hollow probe means adapted for removably connecting the device within the pipeline;

at least one sample aperture means for allowing fluid to flow through the probe means at a velocity substantially equal to a velocity of fluid flow in the pipeline;

piston means mounted within the hollow probe means and defining a passageway extending therethrough, reciprocation of the piston means within the hollow probe means opening and closing the sample aperture means, closing of the sample aperture means isolating a fixed volume of sample within a sample chamber;

sample channel means for carrying the fixed volume of sample from the sample chamber to probe outlet means adapted for connection to an external collection device;

at least one upstream and one downstream opening within the probe means communicating with, respectively, at least one upstream and one downstream channel means for carrying fluid flowing into the at least one upstream and downstream openings to a means for measuring differential pressure between the fluid in the upstream channel and the fluid in the downstream channel; and sensor means communicating with fluid flowing through the probe means for measuring a physical property of the fluid, the measurement of the physical property, the collection of the sample, and the measurement of the differential pressure occurring substantially simultaneously and independently.

7. The device of claim 6 further comprising a flushing tube means mounted within the piston means for flushing the device and for connection of the sensor means thereto.

8. The device of claim 6 wherein the sensor means is used to monitor the temperature of the fluid.

9. The device of claim 6 wherein the sample chamber collects a uniform amount of fluid at selected intervals.

10. The device of claim 6 adapted for connection to a computer means for controlling operation of the device.

11. The device of claim 6 wherein a fluid pressure from the velocity of fluid flow through the probe means opens the sample chamber for delivery of the fixed volume of sample through the sample channel means to the external collection device.

* * * * *

UNITED STATES PATENT AND TRADEMARK OFFICE
CERTIFICATE OF CORRECTION

PATENT NO. : 5,463,908
DATED : November 7, 1995
INVENTOR(S) : Antonio Rosolia

It is certified that error appears in the above-indentified patent and that said Letters Patent is hereby corrected as shown below:

Title page, col. 2, line 1, under Foreign Appliction Priority Data should read --Mar. 30, 1992 [IT] Italy CT 92-000011--.

Signed and Sealed this

Fourth Day of June, 1996

*Attest:*

BRUCE LEHMAN

*Attesting Officer*   Commissioner of Patents and Trademarks